United States Patent [19]

Takasawa et al.

[11] Patent Number: 4,623,722

[45] Date of Patent: Nov. 18, 1986

[54] FORTIMICIN FACTOR $KG_3$

[75] Inventors: Seigo Takasawa, Hadano; Kunikatsu Shirahata, Machida; Seiji Sato, Machida; Keiichi Takahashi, Machida, all of Japan

[73] Assignee: Kyowa Hakko Kogyo Co., Ltd., Tokyo, Japan

[21] Appl. No.: 120,116

[22] Filed: Feb. 11, 1980

Related U.S. Application Data

[62] Division of Ser. No. 17,276, Mar. 5, 1979, Pat. No. 4,241,182.

[30] Foreign Application Priority Data

Mar. 3, 1978 [JP]  Japan ................................. 53-23552

[51] Int. Cl.$^4$ .......................................... C07H 15/224
[52] U.S. Cl. .................................. 536/16.1; 536/16.8
[58] Field of Search ................... 536/17 R, 17 B, 16.1, 536/16.8; 424/180, 181

[56] References Cited

U.S. PATENT DOCUMENTS

| | | | |
|---|---|---|---|
| 4,169,942 | 10/1979 | Mochida et al. | 536/17 B |
| 4,187,299 | 2/1980 | Post | 536/17 B |
| 4,209,612 | 6/1980 | Takahashi et al. | 424/181 |

OTHER PUBLICATIONS

Shirahata et al., American Chemical Society, Washington, DC, 1980, ACS Symposium Series 125, "The Structure of New Fortimicins Having Double Bonds in Their Purpurosamine Moieties".

*Primary Examiner*—Johnnie R. Brown
*Attorney, Agent, or Firm*—Antonelli, Terry & Wands

[57] ABSTRACT

New antibiotic compounds, Fortimicin factors $KG_1$, $KG_2$ and $KG_3$ are produced by fermentation of microorganisms belonging to the genus Micromonospora. The antibiotic compounds are accumulated in the culture liquor and are isolated therefrom.

1 Claim, No Drawings

FORTIMICIN FACTOR KG₃

RELATED APPLICATIONS

This is a division of application Ser. No. 017,276, filed Mar. 5, 1979, now U.S. Pat. No. 4,241,182.

The present invention is related generally to the inventions disclosed in U.S. Pat. No. 3,931,400 issued Jan. 6, 1976 for Fortimicin B and Process For Production Thereof; U.S. Pat. No. 3,976,768 issued Aug. 24, 1976 for Fortimicin A and Process For Production Thereof; U.S. Pat. No. 4,048,015 issued Sept. 13, 1977 for Fortimicin C and Process for Production Thereof; U.S. patent application Ser. No. 845,970, filed Oct. 27, 1977 now U.S. Pat. No. 4,145,253, for Fortimicin Factors D and KE and Processes for Production Thereof; and U.S. patent application Ser. No. 957,845, filed Nov. 6, 1978, now U.S. Pat. No. 4,209,612, for Fortimicin Factors KF and KG and Processes for Production Thereof.

BACKGROUND OF THE INVENTION

The present invention relates to new compositions of matter having antibacterial properties, namely Fortimicin $KG_1$, Fortimicin $KG_2$ and Fortimicin $KG_3$. The invention also pertains to the production of Fortimicin $KG_1$, Fortimicin $KG_2$ and Fortimicin $KG_3$ by culturing a microorganism belonging to the genus Micromonospora, which is capable of producing at least one of the active substances in a nutrient medium, until antibacterial activity is detected in the culture liquor and then isolating at least one of the active substances therefrom.

Antibiotics which exhibit activity against a broad spectrum of bacteria are always in demand. To this end, it has been found that when certain strains of Micromonospora are cultured in a nutrient medium, several antibiotic substances are produced in the culture liquor. Specifically, Fortimicin factors A, B, C, D, KE, KF and KG have been isolated from the culture liquor of *Micromonospora olivoasterospora* MK-70 (ATCC 21819) (FERM-P No. 1560) and have the following structural formulae:

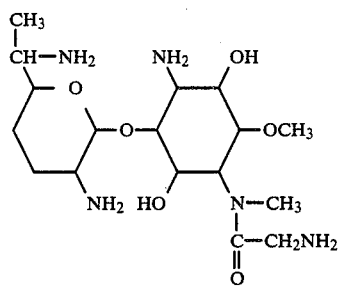

Fortimicin A

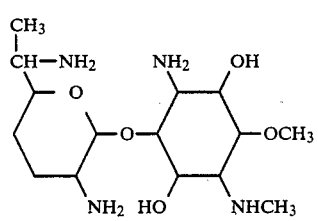

Fortimicin B

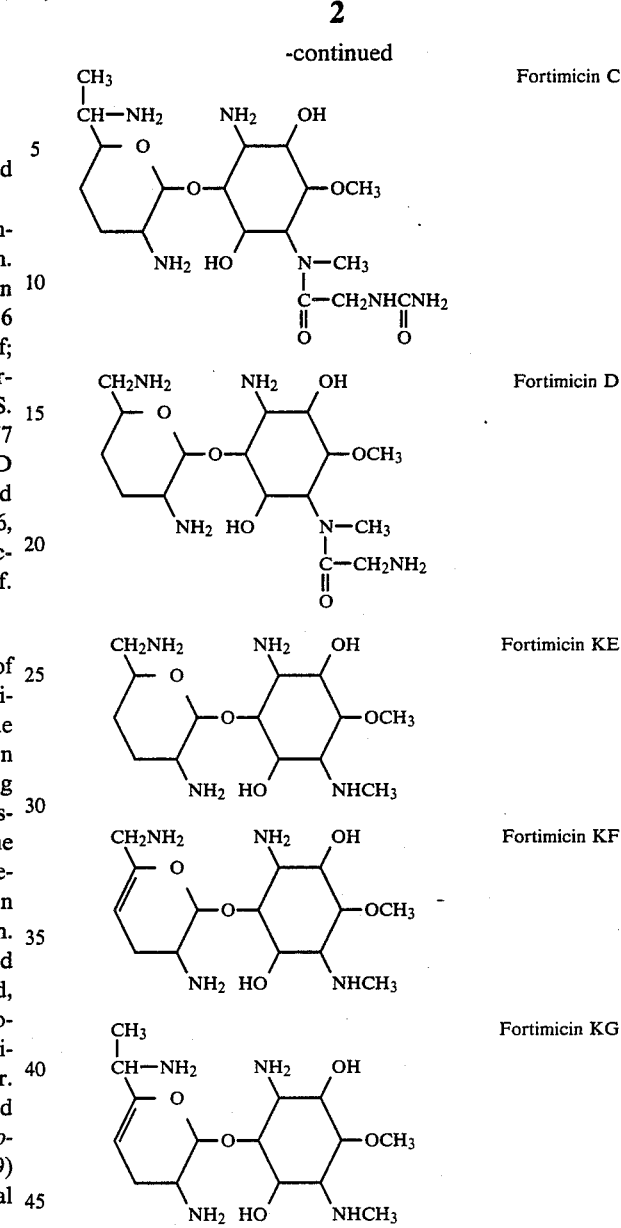

The chemical, physical and biological properties of these antibiotics and the processes for the production thereof are explained in detail in the specifications of the aforementioned United States Patents and Patent applications.

It has now been found that *Micromonospora olivoasterospora* MK-70, when cultured, liberates three further active substances. A study of the chemical, physical and biological properties of these active substances indicates that the compositions of matter are new antibiotics which have now been named Fortimicin $KG_1$, Fortimicin $KG_2$ and Fortimicin $KG_3$.

SUMMARY OF THE INVENTION

In accordance with the present invention, novel antibiotics, Fortimicin factors $KG_1$, $KG_2$ and $KG_3$, are produced by fermentation of a microorganism belonging to the genus Micromonospora which is capable of producing at least one of said factors, in a nutrient medium until substantial antibacterial activity is detected in the culture liquor. At the completion of culturing, the active fractions containing at least one of Fortimicin factors $KG_1$, $KG_2$ and $KG_3$ are isolated from the culture liquor by known means such as by ion exchange resin treatment.

Fortimicin factors $KG_1$, $KG_2$ and $KG_3$ exhibit broad antibacterial activity, and are, therefore, useful inter alia to clean and sterilize laboratory glassware and surgical instruments, and may also be used in combination with soaps, detergents and wash solutions for sanitation purposes. Further, Fortimicin factors $KG_1$, $KG_2$ and $KG_3$ are applicable to medicinal purpose.

Included in the composition of matter aspect of the invention are the pharmaceutically acceptable non-toxic acid addition salts of Fortimicin factors $KG_1$, $KG_2$ and $KG_3$ including the mineral acid addition salts such as hydrochloride, hydrobromide, hydroiodide, sulfate, phosphate, carbonate and nitrate and the organic acid addition salts such as acetate, fumarate, malate, citrate, mandelate, ascorbate, tartarate, succinate and the like.

Such a salt means mono, di, tri or tetra salt formed by the reaction of 1 molecule of Fortimicin factors $KG_1$, $KG_2$ or $KG_3$ with 1–4 equivalent of a pharmaceutically acceptable non-toxic acid.

DETAILED DESCRIPTION OF THE INVENTION

The physiocochemical properties of the free base of Fortimicin $KG_1$ of the present invention are as follows:
(1) A basic white powder
(2) The elementary analytical value found:
  C=52.09%, H=8.81%, N=16.23%
(3) Melting point: 95°–98° C.
(4) Ultraviolet absorption spectrum:
  Ultraviolet absorption spectrum of an aqueous solution of the substance does not show characteristic maximum absorption between 220 nm and 360 nm but only shows terminal absorption.
(5) Specific rotation:
  $[\alpha]_D^{22} = +58.3°$ (c=0.66, $H_2O$)
(6) Infrared absorption spectrum:
  The infrared absorption spectrum is measured in KBr tablet. The free base of Fortimicin $KG_1$ shows maximum absorption at the following wavenumbers (cm$^{-1}$): 3360, 2930, 1675, 1590, 1370, 1110, 1055, 1000
(7) Color reactions:

| Ninhydrin reaction: | positive |
| --- | --- |
| Potassium permanganate reaction: | positive |
| Elson-Morgan's reaction: | negative |
| Biuret reaction: | negative |

(8) The CMR spectrum of Fortimicin $KG_1$ is measured in a deuterium oxide solution (pD=10.7) by using JEOL JNM-100A. The results are as follows:
  δ(ppm) 153.1, 101.2, 95.2, 83.4, 83.2, 75.2, 73.4, 62.2, 60.1, 54.8, 48.9, 47.4, 33.6, 25.7, 20.5
(9) The mass spectrum of the substance reveals the following M ion and fragment ions. The formula in parentheses means the composition formula obtained by high resolution mass spectrometry.
  m/e 346.2218 (M+) ($C_{15}H_{30}N_4O_5$), 247.1543 ($C_{10}H_{21}N_3O_4$), 235.1248 ($C_9H_{19}N_2O_5$), 207.1318 ($C_8H_{19}N_2O_4$), 172.0938 ($C_8H_{14}NO_3$)
  From the result of the mass spectrometry, the molecular weight of the substance is determined to be 346 and the molecular formula is determined to be $C_{15}H_{30}N_4O_5$. The elementary analytical values of the substance as calculated from the molecular formula are C=52.00%, H=8.73% and N=16.17%.

(10) Based on the foregoing physicochemical data, the structural formula of Fortimicin $KG_1$ is considered to be as follows:

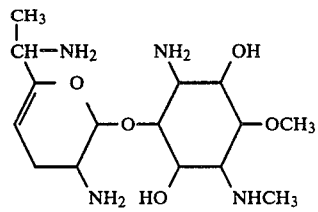

(11) The free base of Fortimicin $KG_1$ is readily soluble in water, soluble in methanol and slightly soluble in ethanol and acetone but is insoluble in organic solvents such as chloroform, benzene, ethyl acetate, butyl acetate, ethyl ether, butanol, petroleum ether, n-hexane, etc.

The physicochemical properties of the free base of Fortimicin $KG_2$ of the present invention are as follows:
(1) A basic white powder
(2) The elementary analytical value found:
  C=52.05%, H=8.80%, N=16.21%
(3) Melting point: 83°–85° C.
(4) Ultraviolet absorption spectrum:
  Ultraviolet absorption spectrum of an aqueous solution of the substance does not show characteristic maximum absorption between 220 nm and 360 nm but only shows terminal absorption.
(5) Specific rotation:
  $[\alpha]_D^{22} = +30°$ (c=0.76, $H_2O$)
(6) Infrared absorption spectrum:
  The infrared absorption spectrum is measured in KBr tablet. The free base of Fortimicin $KG_2$ shows maximum absorption at the following wavenumbers (cm$^{-1}$): 3350, 2920, 1675, 1590, 1370, 1090, 1030, 990
(7) Color reactions:

| Ninhydrin reaction: | positive |
| --- | --- |
| Potassium permanganate reaction: | positive |
| Elson-Morgan's reaction: | negative |
| Biuret reaction: | negative |

(8) The CMR spectrum of the substance is measured in a deuterium oxide solution (pD=10.6) by using JEOL JNM-100A. The results are as follows:
  δ(ppm) 153.1, 101.3, 95.3, 82.2, 80.0, 71.3, 71.1, 61.1, 59.3, 53.8, 48.9, 47.3, 35.4, 25.6, 20.5
(9) The mass spectrum of the substance reveals the following M ion and fragment ions. The formula in parentheses means the composition formula obtained by high resolution mass spectrometry.
  m/e 346.2244 (M+) ($C_{15}H_{30}N_4O_5$), 247.1528 ($C_{10}H_{21}N_3O_4$), 235.1301 ($C_9H_{19}N_2O_5$), 207.1357 ($C_8H_{19}N_2O_4$), 172.0981 ($C_8H_{14}NO_3$)
  From the result of the mass spectrometry, the molecular weight of the substance is determined to be 346 and the molecular formula is determined to be $C_{15}H_{30}N_4O_5$. The elementary analytical values of the substance as calculated from the molecular formula are C=52.00%, H=8.73% and N=16.17%.
(10) Based on the foregoing physicochemical data, the structural formula of Fortimicin KG$_2$ is considered to be as follows:

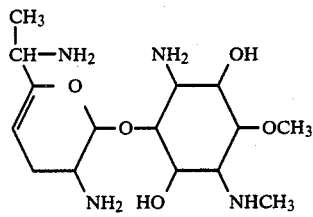

(11) The free base of Fortimicin KG$_2$ is readily soluble in water, soluble in methanol and slightly soluble in ethanol and acetone but is insoluble in organic solvents such as chloroform, benzene, ethyl acetate, butyl acetate, ethyl ether, butanol, petroleum ether, n-hexane, etc.

As is apparent from the foregoing, Fortimicin factors KG$_1$, KG$_2$ and KG (U.S. patent application Ser. No. 957,845, filed Nov. 6, 1978) have the same planer formulae. However, these factors differ from one another in melting point, specific rotation, infrared absorption spectrum and CMR spectrum and therefore, these factors are considered to be stereoisomers with one another. For reference, several physicochemical properties of the free base of Fortimicin KG are shown below:
(1) Melting point: 72°-74° C.
(2) Specific rotation:
   $[\alpha]_D^{24} = +90°$ (c=0.33, H$_2$O)
(3) Infrared absorption spectrum:
   The infrared absorption spectrum is measured in KBr tablet. The free base of Fortimicin KG shows maximum absorption at the following wavenumbers (cm$^{-1}$): 3350, 1678, 1590, 1448, 1365, 1110
(4) The CMR spectrum of the substance is measured in a deuterium oxide solution (pD=10.6) by using JEOL PFT-100A. The results are as follows:
   δ(ppm) 154.1, 101.2, 94.6, 84.5, 79.7, 73.9, 73.3, 62.8, 62.2, 53.4, 48.8, 47.4, 33.9, 25.8, 21.2

The physicochemical properties of the free base of Fortimicin KG$_3$ of the present invention are as follows:
(1) A basic white powder
(2) The elementary analytical value found: C=50.68%, H=8.29%, N=17.45%
(3) Melting point: 135°-138° C.
(4) Ultraviolet absorption spectrum:
   Ultraviolet absorption spectrum of an aqueous solution of the substance does not show characteristic maximum absorption between 220 nm and 360 nm but only shows terminal absorption.
(5) Specific rotation: $[\alpha]_D^{20} = +185°$ (c=0.265, H$_2$O)
(6) Infrared absorption spectrum:
   The infrared absorption spectrum is measured in KBr tablet. The free base of Fortimicin KG$_3$ shows maximum absorption at the following wavenumbers (cm$^{-1}$): 3370, 2940, 1640, 1580, 1462, 1110
(7) Color reactions:

| Ninhydrin reaction: | positive |
| Potassium permanganate reaction: | positive |
| Elson-Morgan's reaction: | negative |
| Biuret reaction: | negative |

(8) The CMR spectrum of the substance is measured in a deuterium oxide solution containing deuteriochloric acid (pD=1.2) by using JEOL JNM-FX100. The results are as follows:
   δ(ppm) 168.8, 146.7, 99.5, 95.9, 76.1, 73.9, 71.4, 66.5, 57.3, 54.2, 52.9, 49.6, 47.2, 41.4, 32.8, 22.2, 16.9
(9) The mass spectrum of the substance reveals the following M ion and fragment ions. The formula in parentheses means the composition formula obtained by high resolution mass spectrometry.
   m/e 403.2490 (M$^+$) (C$_{17}$H$_{33}$N$_5$O$_6$), 304.1750 (C$_{12}$H$_{24}$N$_4$O$_5$), 264.1534 (C$_{10}$H$_{22}$N$_3$O$_5$), 246.1430 (C$_{10}$H$_{20}$N$_3$O$_4$), 100.0723 (C$_5$H$_{10}$NO)
From the result of the mass spectrometry, the molecular weight of the substance is determined to be 403 and the molecular formula is determined to be C$_{17}$H$_{33}$N$_5$O$_6$. The elementary analytical values of the substance as calculated from the molecular formula are C=50.61%, H=8.24%, N=17.36%.
(10) Based on the foregoing physicochemical data, the structural formula of Fortimicin KG$_3$ is considered to be as follows:

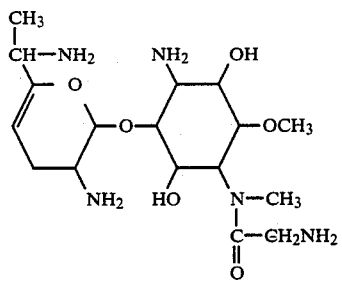

(11) The free base of Fortimicin KG$_3$ is readily soluble in water, soluble in methanol and slightly soluble in ethanol and acetone but is insoluble in organic solvents such as chloroform, benzene, ethyl acetate, butyl acetate, ethyl ether, butanol, petroleum ether, n-hexane, etc.

As apparent from the foregoing, one aspect of the present invention relates eventually to a composition of matter having antibacterial activity which is represented by the general formula I:

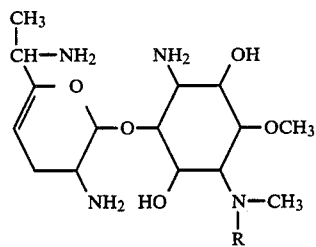

wherein R is

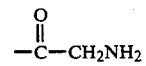

or H and when R is H said composition of matter has the following physicochemical properties:
(1) Melting point: 95°-98° C.,
(2) Specific rotation: $[\alpha]_D^{22} = +58.3°$ (c=0.66, H$_2$O), (3) Infrared absorption spectrum (KBr): 3360, 2930, 1675, 1590, 1370, 1110, 1055 and 1000 cm$^{-1}$ and (4) The CMR spectrum [deuterium oxide solution (pD=10.7)]:

δ(ppm) 153.1, 101.2, 95.2, 83.4, 83.2, 75.2, 73.4, 62.2, 60.1, 54.8, 48.9, 47.4, 33.6, 25.7, 20.5 or the following physicochemical properties:

(1) Melting point: 83°-85° C., (2) Specific rotation: $[\alpha]_D^{22} = +30°$ (c=0.76, H$_2$O), (3) Infrared absorption spectrum (KBr): 3350, 2920, 1675, 1590, 1370, 1090, 1030 and 990 cm$^{-1}$ and (4) The CMR spectrum [deuterium oxide solution (pD=10.6)]:

δ(ppm): 153.1, 101.3, 95.3, 82.2, 80.0, 71.3, 71.1, 61.1, 59.3, 53.8, 48.9, 47.3, 35.4, 25.6, 20.5 and the pharmaceutically acceptable non-toxic acid addition salts thereof.

The Rf values of Fortimicin factors KG$_1$, KG$_2$ and KG$_3$ in paper chromatography and thin layer chromatography are shown in the following Tables 1 and 2. For comparison, the Rf values of antibiotics similar to Fortimicin factors KG$_1$, KG$_2$ and KG$_3$ are also given.

TABLE 1

The Rf values in ascending paper chromatography using as developer the lower layer of chloroform, methanol and concentrated aqueous ammonia (2:1:1 by volume) (at room temperature; after four hours of development)

| Antibiotic | Rf value |
|---|---|
| Fortimicin A | 0.41 |
| Fortimicin B | 0.72 |
| Fortimicin C | 0.22 |
| Fortimicin D | 0.22 |
| Fortimicin KE | 0.63 |
| Fortimicin KF | 0.49 |
| Fortimicin KG | 0.67 |
| Fortimicin KO* | 0.53 |
| Fortimicin KG$_1$ | 0.66 |
| Fortimicin KG$_2$ | 0.70 |
| Fortimicin KG$_3$ | 0.28 |

*Fortimicin KO is disclosed in Japanese Patent application No. 113193/1977, filed September 21, 1977 and has the following structural formula.

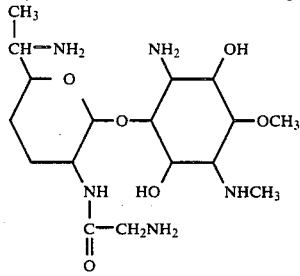

TABLE 2

The Rf values in silica gel thin layer chromatography (at room temperature; after three hours of development; Kieselgel 60 by E. Merck & Co. Inc. is used)

| Antibiotic | Developer I* | Developer II** |
|---|---|---|
| Fortimicin A | 0.36 | 0.09 |
| Fortimicin B | 0.75 | 0.13 |
| Fortimicin C | 0.23 | 0.19 |
| Fortimicin D | 0.21 | 0.06 |
| Fortimicin KE | 0.50 | 0.12 |
| Fortimicin KF | 0.35 | 0.12 |
| Fortimicin KG | 0.55 | 0.12 |
| Fortimicin KO | 0.55 | 0.24 |
| Fortimicin KG$_1$ | 0.58 | 0.14 |
| Fortimicin KG$_2$ | 0.70 | 0.20 |
| Fortimicin KG$_3$ | 0.32 | 0.11 |

*Developer I: The lower layer of chloroform, methanol and concentrated aqueous ammonia (2:1:1 by volume)
**Developer II: 10% (W/V) aqueous ammonium acetate, methanol and concentrated aqueous ammonia (50:50:1 by volume)

Table 3 illustrates the antibacterial spectra of Fortimicin factors KG$_1$, KG$_2$ and KG$_3$ against various microorganisms.

TABLE 3

(Minimum Inhibitory Concentration, μg/ml measured by agar dilution method at pH 8.0)

| Microorganism | Fortimicin KG$_1$ | Fortimicin KG$_2$ | Fortimicin KG$_3$ |
|---|---|---|---|
| Bacillus subtilis No. 10707 | — | — | <0.045 |
| Staphylococcus aureus ATCC 6538P | 13.1 | 10.5 | 0.083 |
| Klebsiella pneumoniae ATCC 10031 | — | — | 0.18 |
| Escherichia coli ATCC 26 | 26.1 | 41.7 | 0.33 |
| Escherichia coli KY8302 (resistant to chloramphenicol, streptomycin, kanamycin, paromomycin, tetracycline and spectinomycin) | 26.1 | 41.7 | 0.52 |
| Escherichia coli KY8327 (resistant to kanamycin, gentamicin and tobramycin) | 26.1 | 20.9 | 0.33 |
| Escherichia coli KY8348 (resistant to streptomycin and gentamicin) | 26.1 | 166.6 | 10.4 |
| Proteus vulgaris ATCC 6897 | 26.1 | 83.3 | 0.66 |
| Shigella sonnei ATCC 9290 | — | — | 0.7 |
| Salmonella typhosa ATCC 9992 | — | — | 0.18 |
| Pseudomonas aeruginosa BMH#1 | >208 | >166.6 | 5.2 |

As is apparent from the above, Fortimicin KG$_3$ has a strong antibacterial activity against a broad range of Gram-positive and Gram-negative bacteria. Particularly, it is characteristic that the antibiotic is effective against certain strains of Escherichia coli which are resistant to various antibiotics. As is also apparent from the above, Fortimicin factors KG$_1$ and KG$_2$ exhibit a broad antibacterial spectrum. Therefore, Fortimicin factors KG$_1$, KG$_2$ and KG$_3$, especially Fortimicin KG$_3$ are expected to have a therapeutic effect on various infections (in human beings and in animals) induced by various bacteria. With such antibacterial properties, Fortimicin factors KG$_1$, KG$_2$ and KG$_3$ are applicable to medicinal purposes. LD$_{50}$ value of Fortimicin KG$_3$ (free base) is determined to be 225 mg/kg in mice by intraveneous administration.

Thus the invention includes within its scope pharmaceutical compositions comprising, as an active ingredient, Fortimicin factor KG$_1$, KG$_2$ or KG$_3$, or a pharmaceutically acceptable non-toxic acid addition salt thereof in association with a pharmaceutical carrier or diluent. The compounds of this invention are administered by parenteral (intramuscular, intraperitoneal, intravenous, intramuscular or subcutaneous injection routes) or rectal routes of administration and can be formulated in dosage forms appropriate for each route of administration.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by beating the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 5 to 300 mg/kg of body weight daily are administered to mammalian patients to achieve an antibiotic effect.

Fortimicin factors $KG_1$, $KG_2$ and $KG_3$ are produced by fermentation of a microorganism belonging to the genus Micromonospora. Any strain belonging to the genus Micromonospora and capable of forming at least one of Fortimicin factors $KG_1$, $KG_2$ and $KG_3$ in the culture liquor may be used. Examples of preferred strains are *Micromonospora olivoasterospora* MK-70 (FERM-P No. 1560) (ATCC 21819), *Micromonospora olivoasterospora* MK-80 (FERM-P No. 2192) (ATCC 31010) and *Micromonospora olivoasterospora* Mm 744 (FERM-P No. 2193) (ATCC 31009). These strains have been deposited with the American Type Culture Collection, Rockville, Md, U.S.A. and with the Fermentation Research Institute Agency of Industrial Science and Technology, Chiba-ken, Japan and have been accorded the accession number noted above.

The microbiological properties of these strains are described in U.S. Pat. No. 3,931,400, which description is expressly incorporated herein by reference.

As is the case with other strains of Actinomycetes, the microorganisms useful in carrying out the present invention can be mutated by artificial means such as ultraviolet irradiation, X-ray irradiation and use of various mutation including chemicals in known manner to enhance the production of metabolic products, an example of which is *Micromonospora olivoasterospora* CS-26 (FERM-P No. 3567, NRRL 8178). This latter mutant has been deposited with the U.S. Dept. of Agriculture, Peoria, Ill., and is freely available to the public.

Generally, conventional methods for culturing Actinomycetes may be employed in the process of the present invention. Thus, various nutrient sources may be used for the culture medium. Appropriate carbon sources include glucose, starch, mannose, fructose, sucrose, molasses, etc. either alone or in combination. Hydrocarbons, alcohols, organic acids, etc. may also be used depending upon the assimilability possessed by the microorganisms to be used. As inorganic and organic nitrogen sources, ammonium chloride, ammonium sulfate, urea, ammonium nitrate, sodium nitrate, may be used either alone or in combination or natural nitrogen sources such as peptone, meat extract, yeast extract, dry yeast, corn steep liquor, soybean powder, casamino acid, soluble vegetable protein, etc. are appropriate. If necessary, inorganic salts such as sodium chloride, potassium chloride, calcium carbonate, phosphates, etc. may be added to the medium. Moreover, organic and inorganic materials which promote the growth of the particular strain and the production of at least one of Fortimicin factors $KG_1$, $KG_2$ and $KG_3$ may be added.

A liquid culturing method, particularly a submerged stirring culturing method is most suitable. Culturing temperature is desirably 25°–40° C., and it is preferred to carry out culturing at around neutral pH. Usually, after 2 to 15 days of liquid culturing, Fortimicin factors $KG_1$, $KG_2$ and $KG_3$ are formed and accumulated in the culture liquor. When substantial antibacterial activity is detected in the culture liquor, preferably when the yield of the antibiotics in the culture liquor reaches a maximum, culturing is discontinued and the desired product is isolated and purified from the culture liquor after the microbial cells have been removed such as by filtration.

Isolation and purification of Fortimicin factors $KG_1$, $KG_2$ and $KG_3$ is carried out by methods usually used for the isolation and purification of microbial metabolic products from a culture liquor.

Since the antibiotics Fortimicin $KG_1$, Fortimicin $KG_2$ and Fortimicin $KG_3$ are basic substances and are readily soluble in water but poorly soluble in the ordinary organic solvents, the antibiotics can be purified by the methods usually used for the purification of so-called water-soluble basic antibiotics. More specifically, the $KG_1$, $KG_2$ and $KG_3$ factors can be purified by a proper combination of adsorption and desorption from cation exchange resin, cellulose column chromatography, adsorption and desorption using a column of Sephadex LH-20, silica gel column chromatography, etc. As an example, a suitable method of purification of Fortimicin factors $KG_1$, $KG_2$ and $KG_3$ from the culture liquor when a strain capable of producing the Fortimicin complex (a mixture containing Fortimicin factors A, B, C, D, KE, KF, KG and KO and by-products having antibacterial activity) is used is as follows. The cell-free culture filtrate is adjusted to pH 7.5 and is then flowed through a cation exchange resin such as Amberlite IRC-50 (ammonium form) (Rohm & Haas Co., U.S.A.). After the resin is washed with water, elution is carried out with 0.5N aqueous ammonia. The active fractions are combined and concentrated under reduced pressure. The concentrate is then flowed through a cation exchange resin, Amberlite CG-50 (ammonium form) (Rohm & Haas Co., U.S.A.). After the resin is washed with water, elution is carried out with 0.1N aqueous ammonia containing 0.1M $NH_4Cl$. First, Fortimicin factors KO and C are eluted and subsequently Fortimicin factors $KG_1$, $KG_2$ and $KG_3$ are eluted together with Fortimicin B. Thereafter, Fortimicin factors A, D, KE, KF and KG are eluted. The fractions containing Fortimicin $KG_1$, $KG_2$ and $KG_3$ are collected, neutralized with hydrochloric acid and flowed through a cation exchange resin such as Amberlite IRC-50 (ammonium form). After the resin is washed with water, elution is carried out with 0.5N aqueous ammonia. The active fractions are collected and concentrated to dryness to obtain a crude powder containing Fortimicin factors $KG_1$, $KG_2$ and $KG_3$. The crude powder is placed on the upper part of a column packed with silica gel. Development is carried out with the lower layer of a mixed solvent of chloroform, methanol and concentrated aqueous ammonia (3:1:1 by volume). First, Fortimicin B which is contained in the crude powder is eluted and subsequently Fortimicin factors $KG_2$, $KG_1$ and $KG_3$ are eluted in this order. The fractions containing respectively Fortimicin factors $KG_1$, $KG_2$ and $KG_3$ are collected, concentrated under reduced pressure and freeze-dried to obtain a respective white free base of Fortimicin factors $KG_1$, $KG_2$ and $KG_3$.

Though fairly pure Fortimicin factors $KG_1$, $KG_2$ and $KG_3$ are obtained by the above treatment, these compounds yet contain a small amount of impurities. Therefore, these compounds are respectively flowed through a cation exchange resin, Bio-Rex-70 (ammonium form) [Bio-Rad Laboratories (U.S.A.)]. After the resin is washed with water, elution is carried out with 0.04N aqueous ammonia containing 0.04M ammonium acetate. The active fractions are collected, neutralized and flowed through Amberlite CG-50 (ammonium form). After the resin is washed with water, elution is carried out with 0.5N aqueous ammonia. The active fractions are collected, concentrated and freeze-dried to obtain a respective pure preparate (free base) of Fortimicin factors $KG_1$, $KG_2$ and $KG_3$.

During the above-described purification procedures, the fractions are checked by silica gel thin layer chromatography. As the developer, the lower layer of a mixed solvent of chloroform, methanol and concentrated aqueous ammonia (2:1:1 by volume) and a mixed solvent of 10% (w/v) aqueous ammonium acetate, methanol and concentrated aqueous ammonia (50:50:1 by volume) are used. Detection is carried out by coloring method using ninhydrin and bioautography using *Bacillus subtilis* No. 10707 as the test microorganism. Rf values of Fortimicin factors $KG_1$, $KG_2$ and $KG_3$ on the silica gel thin layer chromatogram are shown in Table 2.

Certain specific embodiments of the present invention are illustrated by the following representative examples.

EXAMPLE 1

A. Culturing of the MK-70 strain

*Micromonospora olivoasterospora* MK-70 (ATCC 21819) (FERM-P No. 1560) is used as the seed strain. A medium comprising 2 g/dl glucose, 0.5 g/dl peptone, 0.5 g/dl yeast extract and 0.1 g/dl calcium carbonate (pH 7.5 before sterilization) is used as a first seed medium. A loopful of the seed strain is inoculated into 10 ml portions of the first seed medium in 50 ml-large test tubes and is cultured at 30° C. for 5 days. Then, 10 ml of the thus prepared first seed culture is added to 30 ml portions of a second seed medium in 250 ml-Erlenmeyer flasks. The second seed medium has the same composition as that of the first seed medium. The second seed culturing is carried out with shaking at 30° C. for 2 days, and thereafter, 30 ml of the second seed culture is added to 300 ml portions of a third seed medium in 2 l-Erlenmeyer flasks provided with baffles. The third seed medium is of the same composition as that of the first seed medium. The third seed culturing is carried out with shaking at 30° C. for 2 days. Then, 1.5 l of the third seed culture (corresponding to 5 flasks) is added to 15 l of a fourth seed medium in a 30 l-stainless steel jar fermenter. The fourth seed medium has the same composition as that of the first seed medium. The fourth seed culturing in the jar fermenter is carried out with aeration and stirring (revolution: 350 r.p.m.; aeration: 15 l/min) at 37° C. for 2 days. Then, 15 l of the fourth seed culture is added to 150 l of a fermentation medium in a 300 l-fermenter. The fermentation medium has the following composition:

| Soluble starch | 4 g/dl | $K_2HPO_4$ | 0.05 g/dl | $CaCO_3$ | 0.1 g/dl |
|---|---|---|---|---|---|
| Soybean meal | 2 g/dl | $MgSO_4.7H_2O$ | 0.05 g/dl | | |
| Corn steep liquor | 1 g/dl | KCl | 0.03 g/dl | | |
| (pH 7.5 before sterilization) | | | | | |

Fermentation in the fermenter is carried out with aeration and stirring (revolution: 150 r.p.m.; aeration: 80 l/min) at 37° C. for 4 days.

B. Isolation of crude Fortimicin complex containing $KG_1$, $KG_2$ and $KG_3$ After the completion of fermentation, the culture liquor is adjusted to pH 2.5 with concentrated sulfuric acid and is stirred for 30 minutes. Thereafter, about 7 kg of a filter aid, Radiolite No. 600 (product of Showa Kagaku Kogyo Co., Ltd., Japan) is added to the culture liquor and the microbial cells are removed by filtration. The filtrate is adjusted to pH 7.5 by the addition of 6N sodium hydroxide, and then flowed through a column packed with about 20 l of a cation exchange resin, Amberlite IRC-50 (ammonium form). The active principles are adsorbed on the resin, and the effluent is discarded. After the resin is washed with water, elution of the active principles is carried out with 1N aqueous ammonia. The eluate is subjected to determination of activity by a paper disc method using an agar plate of *Bacillus subtilis* No. 10707. Fractions showing an activity are combined and concentrated under reduced pressure to about 1 l. The concentrate is adjusted to pH 7 with concentrated hydrochloric acid and then flowed through a column packed with 3 l of Amberlite CG-50 (ammonium form). After the resin is washed with water, elution is carried out with 0.1N $NH_4OH$ containing 0.1M $NH_4Cl$. The eluate is taken in 500 ml fractions. Each fraction is subjected to determination of antibacterial activity against *Bacillus subtilis* No. 10707 and identification of active component by silica gel thin layer chromatography [Developer: the lower layer of a mixed solvent of chloroform, methanol and concentrated aqueous ammonia (2:1:1 by volume), Coloring agent: ninhydrin]. After the volume of the eluate reaches about 3 l, Fortimicin factors $KG_1$, $KG_2$ and $KG_3$ begin to be eluted. The fractions containing Fortimicin factors $KG_1$, $KG_2$ and $KG_3$ are collected, concentrated under reduced pressure to remove ammonia, neutralized with concentrated hydrochloric acid and flowed through a column packed with 500 ml of Amberlite IRC-50 (ammonium form). After the resin is washed with water, elution is carried out with 0.5N aqueous ammonia. The active fractions are collected, concentrated under reduced pressure and freeze-dried to obtain 2 g of a white powder. The powder contains in it 250 mg of Fortimicin $KG_1$, 640 mg of Fortimicin $KG_2$ and 330 mg of Fortimicin $KG_3$.

C. Respective isolation and purification of Fortimicin factors $KG_1$, $KG_2$ and $KG_3$ 2 g of the crude powder is placed on a silica gel column (Silica gel: produced by Wako Junyaku Co., Ltd., Japan, Diameter of column: about 3 cm). Development is carried out with the lower layer of a mixed solvent of chloroform, methanol and concentrated aqueous ammonia (3:1:1 by volume). The eluate is taken in 20 ml fractions. Each fraction is subjected to the silica gel thin layer chromatography. First, Fortimicin B is eluted and then Fortimicin factors $KG_2$, $KG_1$ and $KG_3$ are eluted in this order. The fractions respectively containing Fortimicin factors $KG_1$, $KG_2$ and $KG_3$ are collected, concentrated under reduced pressure and freeze-dried to obtain 200 mg of Fortimicin $KG_1$, [Activity: 970 u/mg (u: unit)], 500 mg of Fortimicin $KG_2$ (Activity: 970 u/mg) and 250 mg of Fortimicin $KG_3$ (Activity: 950 u/mg) (Activity of each of the purified substances is considered to be 1000 u/mg).

200 mg of the thus obtained Fortimicin $KG_1$ is dissolved in water. The solution is adjusted to pH 7.0 and flowed through a column packed with 50 ml of Bio-Rex-70 (ammonium form). After the resin is washed with water, elution is carried out with 0.04N aqueous ammonia containing 0.04M ammonium acetate. The eluate is taken in 10 ml of fractions and each fraction is subjected to the silica gel thin layer chromatography. The fractions containing only Fortimicin $KG_1$ are collected, concentrated under reduced pressure to remove ammonia, adjusted to pH 7.0 and flowed through a column packed with 100 ml of Amberlite IRC-50 (ammonium form). After the resin is washed with water, elution is carried out with 0.5N aqueous ammonia. The active fractions are collected, concentrated under reduced pressure and freeze-dried to obtain 150 mg of a free base of pure Fortimicin $KG_1$ as a white powder.

500 mg of Fortimicin $KG_2$ and 250 mg of Fortimicin $KG_3$ respectively obtained by the above silica gel chromatography are treated in the same manner as above-described with Fortimicin $KG_1$ to obtain 470 mg of a free base of pure Fortimicin $KG_2$ and 230 mg of a free base of pure Fortimicin $KG_3$ respectively as a white powder.

EXAMPLE 2

*Micromonospora olivoasterospora* Mm 744 (ATCC 31009) (FERM-P No. 2193) is used as the seed strain. A medium comprising 2 g/dl glucose, 0.5 g/dl peptone, 0.3 g/dl yeast extract and 0.1 g/dl calcium carbonate (pH 7.2 before sterilization) is used as a first seed medium. The seed culture (the first seed culture—the fourth seed culture) is carried out in the same manner as described in the Example 1. The composition of the second seed medium—the fourth seed medium is the same as that of the first seed medium. 15 l of the thus obtained fourth seed culture is added to 150 l of a fermentation medium in a 300 l-stainless steel fermenter. The fermentation medium has the following composition:

| Soluble starch | 2 g/dl | $K_2HPO_4$ | 0.05 g/dl |
|---|---|---|---|
| Soybean meal | 0.5 g/dl | $MgSO_4.7H_2O$ | 0.05 g/dl |
| Glucose | 2 g/dl | KCl | 0.03 g/dl |
| Corn steep liquor | 1 g/dl | $CaCO_3$ | 0.1 g/dl |
| Yeast extract | 1 g/dl | | |

-continued
(pH 7.0 before sterilization)

Fermentation in the fermenter is carried out with aeration and stirring (revolution: 150 r.p.m.; aeration: 80 l/min) at 30° C. for 4 days.

After the completion of fermentation, the culture liquor is subjected to the same purification and isolation method as described in the Example 1 to obtain 120 mg of a free base of pure Fortimicin $KG_1$, 350 mg of a free base of pure Fortimicin $KG_2$ and 180 mg of a free base of pure Fortimicin $KG_3$.

EXAMPLE 3

*Micromonospora olivoasterospora* MK 80 (ATCC 31010) (FERM-P No. 2192) is used as the seed strain. A medium comprising 1 g/dl glucose, 1 g/dl soluble starch, 0.5 g/dl yeast extract, 0.5 g/dl peptone and 0.1 g/dl calcium carbonate (pH 7.0 before sterilization) is used as a first seed medium. The seed culture (the first seed culture—the fourth seed culture) is carried out in the same manner as described in the Example 1. The composition of the second seed medium—the fourth seed medium is the same as that of the first seed medium. The thus obtained fourth seed culture is subjected to fermentation in the same manner as described in the Example 1. The fermentation medium has the same composition as that of the fermentation medium described in the Example 1.

After the completion of fermentation, the culture liquor is subjected to the same purification and isolation method as described in the Example 1 to obtain 130 mg of a free base of pure Fortimicin $KG_1$, 390 mg of a free base of pure Fortimicin $KG_2$ and 200 mg of a free base of pure Fortimicin $KG_3$.

EXAMPLE 4

In this example, the same procedure as described in the Example 1 is repeated except that *Micromonospora olivoasterospora* CS-26 (NRRL 8178) (FERM-P No. 3567), which is a mutant strain derived from *Micromonospora olivoasteropora* MK-70 (ATCC 21819) (FERM-P No. 1560) by means of treatment with nitrosoguanidine, ultraviolet irradiation and $\gamma$-ray irradiation, is used as the seed strain. As the result, 170 mg of a free base of pure Fortimicin $KG_1$, 450 mg of a free based of pure Fortimicin $KG_2$ and 280 mg of a free base of pure Fortimicin $KG_3$ are obtained.

EXAMPLE 5

In this example, each 1 g of the free base of Fortimicin factors $KG_1$, $KG_2$ and $KG_3$ is dissolved in a small amount of water. The solution is adjusted to pH 4.5 with 6N-sulfuric acid. To the solution is added about 10 times the volume of the solution of acetone to precipitate respectively sulfates of Fortimicin factors $KG_1$, $KG_2$ and $KG_3$. The precipitate is taken by centrifugation and dried to obtain about 1.6 g of sulfate of Fortimicin $KG_1$ (620 u/mg), about 1.6 g of sulfate of Fortimicin $KG_2$ (620 u/mg) and about 1.5 g of sulfate of Fortimicin $KG_3$ (650 u/mg) respectively as a white powder.

What is claimed is:

1. Fortimicin $KG_3$, a composition of matter which has antibacterial activity, the structural formula:

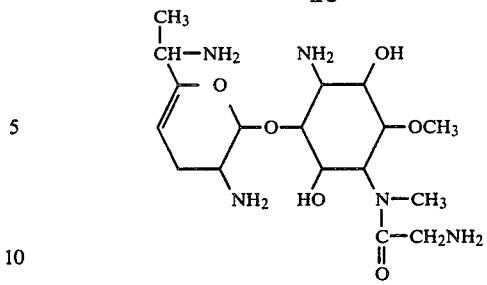
and the following physicochemical properties:
(1) Melting point: 135°–138° C.,
(2) Specific rotation: $[\alpha]_D^{20} = +185°$ (c=0.265, $H_2O$),
(3) Infrared absorption spectrum (KBr): 3370, 2940, 1640, 1580, 1462, 1110 $cm^{-1}$ and
(4) The CMR spectrum [deuterium oxide solution containing deuteriochloric acid (pD=1.2)]: δ(ppm): 168.8, 146.7, 99.5, 95.9, 76.1, 73.9, 71.4, 66.5, 57.3, 54.2, 52.9, 49.6, 47.2, 41.4, 32.8, 22.2, 16.9.
* * * * *